(12) United States Patent
Jonkers

(10) Patent No.: US 8,460,458 B2
(45) Date of Patent: Jun. 11, 2013

(54) HEALING AGENT IN CEMENT-BASED MATERIALS AND STRUCTURES, AND PROCESS FOR ITS PREPARATION

(75) Inventor: Hendrik Marius Jonkers, Delfgauw (NL)

(73) Assignee: Technische Universiteit Delft, Delft (NL)

( * ) Notice: Subject to any disclaimer, the term of this patent is extended or adjusted under 35 U.S.C. 154(b) by 0 days.

(21) Appl. No.: 13/452,524

(22) Filed: Apr. 20, 2012

(65) Prior Publication Data

US 2012/0199046 A1 Aug. 9, 2012

Related U.S. Application Data

(60) Division of application No. 12/841,581, filed on Jul. 22, 2010, now abandoned, which is a continuation of application No. PCT/NL2009/050025, filed on Jan. 22, 2009.

(30) Foreign Application Priority Data

Jan. 23, 2008 (EP) ..................................... 08100833

(51) Int. Cl.
*C04B 7/00* (2006.01)
*C04B 14/00* (2006.01)
*C04B 24/00* (2006.01)
*C04B 24/10* (2006.01)
*C04B 12/02* (2006.01)
*C04B 28/34* (2006.01)
*C04B 7/32* (2006.01)
*C04B 7/36* (2006.01)
*C04B 9/11* (2006.01)
*C04B 11/28* (2006.01)
*C04B 28/06* (2006.01)
*C04B 18/06* (2006.01)
*C04B 16/00* (2006.01)
*C12N 11/00* (2006.01)
*C12N 11/16* (2006.01)
*C12N 11/14* (2006.01)

(52) U.S. Cl.
USPC ........... 106/724; 106/608; 106/691; 106/696; 106/708; 106/802; 435/174; 435/176

(58) Field of Classification Search
USPC .. 106/608, 691, 696, 708, 724, 802; 435/174, 435/176
See application file for complete search history.

(56) References Cited

U.S. PATENT DOCUMENTS

| 5,395,808 A * | 3/1995 | Miller et al. ...................... 502/7 |
| 6,258,589 B1 | 7/2001 | Dybas et al. |
| 6,290,769 B1 * | 9/2001 | Carkner ........................ 106/675 |
| 2006/0148633 A1 | 7/2006 | Kuhn et al. |
| 2008/0245272 A1 | 10/2008 | Kucharski et al. |
| 2011/0011303 A1 | 1/2011 | Jonkers |

FOREIGN PATENT DOCUMENTS

| EP | 0758633 | 2/1997 |
| WO | WO 2004065328 | 8/2004 |
| WO | WO 2006066326 | 6/2006 |

OTHER PUBLICATIONS

Maydl, Peter. "Determination of particle desnity of lightweight aggregates with porous surface". Materials and Structures. 1988. Issue 21. pp. 394-397.*
AQUACLAY, "Biological Filtration-Water Purification", www.aquaclay.com.au.
ARGEX, "Products, Applications, Concrete", www.argex.eu/en/applications.
ARGEX Brochure, "Concrete, clay aggregates, applications", www.argex.be.
Bang, Sookie S. et al., "Calcite Precipitation Induced by Polyurethane-Immobilized *Bacillus pasteurii*", Enzyme and Microbial Technology, vol. 28, 2001, pp. 404-409.
De Muynck, W. et al., "Improvement of Concrete Durability with the Aid of Bacteria", Noordwijk aan Zee, The Netherlands, Apr. 18, 2007, pp. 1-11.
De Muynck, W. et al., "Improvement of Concrete Durability with the Aid of Bacteria", Proceedings of the First International Conference on Self Healing Materials, Apr. 18, 2007, pp. 1-11.
De Muynck, W. et al., "Microbial Ureolytic Calcium Carbonate Precipitation for Remediation of Concrete Surfaces", International Conference on Concrete Repair, Rehabilitation, and Retrofitting, Alexander, M. (ed), Nov. 21, 2005, pp. 785-790.
Jonkers, Henk M. et al., "Crack Repair by Concree-Immobilized Bacteria", Noordwijk aan Zee, The Netherlands, Apr. 18, 2007, pp. 1-7.
Jonkers, Henk M. et al., "Crack Repair by Concree-Immobilized Bacteria", Proceedings of the First International Conference on Self Healing Materials, Apr. 18, 2007, pp. 1-7.
Jonkers, Henk M. et al., "Development of a Bacteria-Based Self Healing Concrete", Tailor Made Concrete Structures, Walraven & Stoelhorst (eds), 2008, pp. 425-430.

(Continued)

*Primary Examiner* — Kaj K Olsen
*Assistant Examiner* — Karam Hijji
(74) *Attorney, Agent, or Firm* — Jeffrey D. Myers; Janeen Vilven; Isaac Estrada

(57) ABSTRACT

A process for the preparation of the healing agent in cement-based materials and structures, wherein said healing agent comprises organic compounds and/or bacteria-loaded porous particles, which porous particles comprise expanded clay- or sintered fly-ash. Furthermore, said porous particles are intact spheres, broken or crushed particles derived from said intact spheres, having a specific density between 0.4 and 2 g cm$^{-3}$.

14 Claims, No Drawings

OTHER PUBLICATIONS

Jonkers, Henk M., "Self-Healing Concree: A Biological Approach", S. van der Zwaag (ed.), Self Healing Materials. An Alternative Approach to 20 Centuries of Materials Science, 2007, pp. 195-204.

Jonkers, Henk M. et al., "Self-Healing of Cracked Concete: A Bacterial Approach", Fracture Mechanics of Concrete and Concrete Structures—High Performance Concrete, Brick-Masonry and Environmental Aspects, Carpinteri, et al. (eds), 2007, pp. 1821-1826.

LIAPOR, , "Lightweight Concrete", www.liapor.com/en/structural.

LYTAG, , "Lightweight aggregates, fills and concrete", www.lytag.net/about.

Pirog, T. P. et al., "Use of Claydite-Immobilized Oil-Oxidizing Microbial Cells for Purification of Water from Oil", Priki Biokhim Mikrobiol, vol. 41 (1), Abstract of article in Russian, Jan.-Feb. 2005, pp. 58-63.

Ramachandran, Santhosh K. et al., "Remediation of Concrete Using Micro-Organisms", ACI Materials Journal-Technical Paper, Jan.-Feb. 2001, pp. 3-9.

Ramakrishnan, V. et al., "Bacterial Concrete", Smart Materials, Proceedings of SPIE, vol. 4234, 2001, pp. 168-176.

* cited by examiner

HEALING AGENT IN CEMENT-BASED MATERIALS AND STRUCTURES, AND PROCESS FOR ITS PREPARATION

CROSS-REFERENCE TO RELATED APPLICATIONS

This application is a Divisional application of U.S. Ser. No. 12/841,581 filed Jul. 22, 2010 which is a continuation application of International Patent Application Ser. No. PCT/NL2009/050025 entitled "Healing Agent in Cement-Based Materials and Structures, and Process for its Preparation", to Technische Universiteit Delft, filed on Jan. 22, 2009, which is a continuation of European Patent Application Ser. No. 08100833.6, entitled "Healing Agent in Cement-Based Materials and Structures, and Process for its Preparation", to Technische Universiteit Delft, filed on Jan. 23, 2008, and the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND OF THE INVENTION

1. Field of the Invention

The present invention relates to a healing agent in cement-based materials and structures, as well as to a process for its preparation.

2. Description of Related Art

Porous aggregate material (expanded clay- or sintered fly-ash) loaded with bio-chemical compounds (bacteria and/or organic compounds) can improve the durability of cement-based structures when incorporated in the material matrix. Porous materials such as different types of expanded clays (brand name, e.g., Liapor®, Argex®) and fly-ash (sintered pulverized coal ash) (e.g., Lytag®) are commonly applied as aggregate material in cement-based materials, specifically for the production of lightweight concrete. So far, however, the potential storage capacity of these porous materials for healing or repair agents, such as chemical compounds or bacteria, have not been proposed or applied yet.

In recent years, the application of bacteria for the improvement and/or repair of cement-based materials, and concrete in particular, have been investigated in several studies (Bang et al. 2001; Ramachandran et al. 2001; DeMuynck et al. 2005 and 2007; Jonkers & Schlangen 2007a+b; Jonkers 2007). In some of these studies bacteria, or derived enzymes, were applied externally, i.e., as a surface treatment system, to plug, seal, or heal cracks in concrete through metabolic or enzymatic biomineral formation. In only few reported studies bacteria were truly incorporated in the concrete matrix (e.g. by mixing with the still fluid cement paste), to investigate their potential for autonomous improvement of concrete characteristics, e.g. to act as concrete-immobilized self-healing agent (Jonkers & Schlangen 2007a+b; Jonkers 2007).

Major disadvantage of direct addition of bacteria or their spores to cement paste is that this procedure may strongly decrease their viability [Jonkers & Schlangen 2007b]. Reason for the limited life-time of bare concrete immobilized bacteria is most likely a combination of high concrete matrix alkalinity (pH>12) and ongoing reduction in matrix pore-size diameter (<1 µm) during continued cement hydration.

BRIEF SUMMARY OF THE INVENTION

The object of the present invention is to provide a healing agent in cement-based materials and structures, wherein the above-mentioned disadvantages are eliminated.

This goal has been achieved by the present invention by providing a healing agent in cement-based materials and structures wherein said healing agent comprises organic compounds and/or bacteria-loaded porous particles.

BRIEF DESCRIPTION OF THE SEVERAL VIEWS OF THE DRAWINGS

Not Applicable.

DETAILED DESCRIPTION OF THE INVENTION

Usually the porous particles comprise expanded clay- or sintered fly-ash and they can occur as intact spheres, broken or crushed particles derived from intact spheres.

The specific density of said porous particles is between 0.4 and 2 g cm$^{-3}$.

Furthermore, the surface pore has a width of 1.0 to 100 µm, and preferably between 1.0 and 15 µm.

It is advantageous according to the invention when the size of the bacteria-only loaded particles have a particle size with a diameter of >0.02 mm, preferably 0.02-8 mm. Commonly, the particle size of the bacteria-only loaded particles is 0.05 mm.

Usually, the bacterial spores or species according to the invention belong to the genera *Bacillus* and *Sporosarcina*, whereas preferably as bacteria *Bacillus pseudofirmus* is used.

On the one hand, bacteria belonging to the genus *Sporosazcina* are ureolytic bacteria, such as *Sporosarcina pasteurii*.

On the other hand, the organic compound is a chemical biomineral precursor compound, preferably calcium formate, calcium acetate, or other carboxylic acid calcium salt.

Last but not least it is advantageous that the particle surface pore has a width of 0.01-1 µm for biomineral precursor compound-loaded particles.

It appeared surprisingly according to the invention that when protecting the bacteria or their spores by immobilization inside expanded clay- or sintered fly-ash particles prior to addition to cement paste can result in almost full preservation, or significantly diminished decrease in viability, and thus to a longer-term potential as healing or repair agent in concrete and other cement-based materials.

In addition to bacteria, porous expanded clay- or expanded fly-ash particles can also be loaded with a suitable organic biomineral precursor compound to increase the healing or repair potential of these particles in concrete and cement-based materials.

In order to obtain a favorable result, the porous particle characteristics such as specific density, size, surface pore-size and applied density in cement-based materials are as follows.

Usually, expanded clay- or sintered fly-ash particles can be intact spheres.

Furthermore, the surface pore width dimensions are important as these should be large enough to allow bacteria to enter.

The choice of applied particle size, its surface pore width and applied density in the cement-based material depends mainly on the intended functionality of the loaded particle. A particle can be small when loaded with bacteria (i.e., catalyst for biomineral production) only, but needs to be rather large when additionally loaded with the chemical biomineral precursor compound needed for healing of the cement-based material. The first option is feasible when the biomineral precursor compound will be applied externally, i.e., will be provided to the bacteria via intrusion through cracks in the material. In this case, bacteria-only loaded particles can be small and the distribution and applied density of the particles should be such that the chance that a newly formed microcrack in the cement-based material encounters a matrix embedded porous bacteria-loaded particle is significant. For this application, porous particle surface pore width should not be too large, i.e., to prevent substantial leakage of previously intruded bacteria before setting of the cement paste. Therefore, surface pore width should be between 1.0 and 100 µm, or more ideally between 1.0 and 15 µm. The size of bacteria-only loaded particles should be large enough to accommodate and protect a substantial number of bacteria or bacterial spores, i.e., a particle size with a diameter of minimally 0.02 mm. The chance that a newly formed crack with a crack width of 0.1 mm and a length of 2 mm encounters a 0.05 mm diameter bacteria-loaded particle is close to one when the particles are homogeneously distributed through the material. The volumetric ratio of 0.05 mm sized particles to the cement-based material would then be in the order of 1:240. However, particle sizes may also be larger, i.e., in the range of 0.02 to 8 mm. Furthermore, when the porous particles should also function as a reservoir for chemical biomineral precursor compounds, sizes should be substantially larger than 0.02 mm, as the volumetric healing or repair potential of such chemicals are directly related to their own volume. The healing, or crack-filling, potential is limited to the amount of healing agent loaded in porous particles, i.e., the larger the to-be-healed crack volume, the larger the porous particle reservoir volume must be. Note that less volume is needed when the conversion reaction of precursor compound to produced biomineral is an expansive reaction. Also, partial biomineral crack plugging may already result in a substantial reduction, thus healing, of crack permeability. Reservoir particles should therefore not be too small as this would limit their healing or repair potential. However, their size should also not be too large, as the distribution and amount of the particles should be such that the compressive strength and related functionality of the cement-based material is not negatively affected to a major extend. The particle surface pore width of chemical biomineral precursor compound-loaded particles should be similar to those of bacteria-loaded particles when both are simultaneously loaded. However, particle surface pore width can be substantially smaller, i.e., in the range of 0.01 to 1 µm, when the suitable chemical biomineral precursor compound is loaded to the porous particles without additional bacteria. For the latter material healing or repair application two different types of porous particles may thus be applied simultaneously, i.e., one loaded with bacteria or their spores, and the other with a suitable chemical biomineral precursor compound.

Furthermore, the present invention relates to a process for the preparation of the healing agent as described above.

Accordingly, the present invention relates to a process for the preparation of the healing agent characterized in that the porous aggregate material, expanded clay- or sintered fly-ash, is loaded with bacteria and/or organic compounds by contacting said porous particle with the bacteria or bacterial spore-containing suspension or chemical biomineral precursor compound solution, wherein first the porous particles are dried and freed from the viable environmental bacteria by drying the same overnight in an oven at a temperature of 120-200° C., preferably 140° C., followed by cooling to room temperature, subjecting the particles to vacuum treatment, while the porous particles still under vacuum the bacteria or bacterial spore-containing suspension or chemical biomineral precursor compound solution is supplied to the particles and the particles are fully submerged, releasing the partial vacuum followed by drying said suspension or solution-entrained particles at room temperature and storing the same at room temperature until further use.

The above process is suitable for loading the porous particles with the bacteria- or bacterial spore-containing suspension or chemical biomineral precursor compound solution. It should be noted when the partial vacuum is subsequently released, the suspension or solution will efficiently intrude the porous particles.

According to the present process, especially bacterial spores of species related to the genera *Bacillus* and *Sporosarcina* can be kept viable for several years. Also, bacterial spores of species of these genera will remain viable for months up to several years when incorporated in cement-based materials such as concrete when immobilized inside porous particles prior to mixing with fresh (non-set) cement paste.

It is noted that for a long-term (several years) healing potential, the number of porous particle-immobilized bacterial spores should be in the range of $10^4$ to $10^9$ spores cm$^{-3}$ concrete.

Herein after the present invention will be further illustrated by the following not-limitative examples.

Example 1

Application of expanded clay particles loaded with *Bacillus pseudofirmus* spores and calcium lactate solution to decrease permeability of cracked concrete.

The produced spores of a *Bacillus pseudofirmus* DSM 8715 culture in its late exponential growth phase are harvested by centrifugation (20 minutes at 10000 g). The obtained pellet, containing cells and spores, is washed once by re-suspension of the pellet in tap water followed by an additional centrifugation step. The washed pellet is subsequently re-suspended in an aliquot of tap water to obtain a suspension with a density of $3 \cdot 10^{10}$ spores ml$^{-1}$. A batch of crushed expanded clay particles (e.g. Liapor®, Liapor GmbH & Co. KG Hallendorf, Germany) with an average particle size of 0.05 mm is dried overnight at a temperature of about 140° C. followed by cooling to room temperature. An amount of this batch is subsequently brought under partial vacuum, after which 1 ml of a $3 \cdot 10^{10}$ spores ml$^{-1}$ spore suspension is added per 16.5 g of evacuated particles, where after the vacuum is released. The spore suspension-intruded porous particles are subsequently dried at a temperature of 30° C. until no further weight loss occurs. A second batch of intact expanded clay spheres (e.g. Aquaclay®, Okotau Easy Green GmbH, Germany) in the size range of 4-8 mm is dried overnight at a temperature of about 140° C. followed by cooling to room temperature. An amount of this batch is subsequently brought under partial vacuum, after which a 150 mM calcium lactate solution is added until all evacuated particles are submerged, where after the vacuum is released. The calcium lactate solution-intruded porous intact spheres are subsequently dried at a temperature of 30° C. until no further weight loss occurs. Aggregate fractions, cement and water are mixed according to the following specifications.

| Aggregate size (mm) | Type | Density (g/cm³) | Weight (g) | Volume cm³ |
|---|---|---|---|---|
| 4-8 | Aquaclay ® + Ca-Lactate | 1.1 | 687 | 624 |
| 2-4 | Sand | 2.7 | 1133 | 420 |
| 1-2 | Sand | 2.7 | 848 | 314 |
| 0.5-1 | Sand | 2.7 | 848 | 314 |
| 0.25-0.5 | Sand | 2.7 | 730 | 270 |
| 0.125-0.25 | Sand | 2.7 | 396 | 147 |
| 0.05 | Liapor ® + B. pseudofirmus spores | 1.3 | 17 | 13 |
| OPC CEMI 32.5R | Cement | 3.15 | 1170 | 371 |
| Water | Water | 1.0 | 585 | 585 |

The crushed Liapor®-immobilized B. pseudofirmus spores in this type of concrete are characterized by a long-term viability (months to years). Germinating spores, activated by water penetrating freshly formed cracks, can mediate the production of calcite by the metabolic conversion of calcium lactate and concrete matrix portlandite according to the following reaction:

$$Ca(C_3H_5O_3)_2 + 5Ca(OH)_2 + 6O_2 \rightarrow 6CaCO_3 + 10H_2O$$

The produced calcite decreases concrete permeability by sealing freshly formed cracks.

Example 2

Application of expanded clay particles loaded with *Sporosarcina pasteurii* spores as healing agent in concrete.

In this example expanded clay particle-immobilized spores of ureolytic bacteria such as *Sporosarcina pasteurii* DSM 33 act as healing catalyst in cracked concrete, while the calcite precursor compound mixture (a mixture of urea, calcium acetate and peptone) is applied externally. The produced spores of a *Sporosarcina pasteurii* DSM 33 culture are immobilized in expanded crushed clay (e.g., Liapor®) particles using the procedure as described under example 1. The 0.05 mm sized *S. pasteurii* spore-containing particles ($1.8 \cdot 10^9$ spores/gram particles) are added to the concrete mixture in a proportion of 5.4 kg per 1 m³ concrete mixture. Surface cracks in set and aged concrete can subsequently be healed by immersion or spraying the concrete surface with the urea, calcium acetate, peptone mixture (10, 27 and 0.5 g/L water respectively). The organics acetate and peptone of this mixture will activate (germinate) the *S. pasteurii* spores which ureolytic activity will subsequently result in the hydrolysis of urea. The carbonate ions produced by this reaction will spontaneously precipitate with the solution's calcium ions to produce a dense and relatively impermeable calcite layer within cracks and on the concrete surface. Instead of applying the calcite precursor compound mixture externally, it can also be absorbed into porous expanded clay particles which are added to the concrete mixture, analogous to the procedure described in Example 1, in order to obtain an autonomous bacterially-mediated calcite producing system.

It should be noted that the present invention is not limited to the above examples and that other embodiments within the skill of the ordinary men in the art belong to the invention as well.

What is claimed is:

1. A process to decrease permeability of cracked concrete, the process comprising:
   providing a healing agent wherein said healing agent comprises either porous particles loaded with bacterial spores and organic compounds or a combination of a first set of porous particles loaded with bacterial spores and a second set of porous particles loaded with organic compounds;
   adding said healing agent to concrete; and
   activating the healing agent with water.

2. The process according to claim 1, wherein said porous particles comprise expanded clay or sintered fly ash.

3. The process according to claim 1, wherein said porous particles are intact spheres or broken or crushed particles derived from said intact spheres.

4. The process according to claim 1, wherein the specific density of said porous particles is between 0.4 and 2 g cm⁻³.

5. The process according to claim 1, wherein the surface pores have a width of 0.01 to 100 μm.

6. The process according to claim 5, wherein the surface pores have a width of 0.01 and 15 μm.

7. The process according to claim 1, wherein the particles of the first set have a diameter of >=0.02 mm.

8. The process according to claim 7, wherein the porous particles of the first set have a diameter of 0.02 mm to 8 mm.

9. The process according to claim 8, wherein the porous particles of the first set have a diameter of 0.05 mm to 1.0 mm and surface pores with a width of 1.0 to 15 μm.

10. The process according to claim 1, wherein said bacterial spores belong to the genera *Bacillus* or *Sporosarcina* and comprise either vegetative bacteria or their spores or a combination of the two.

11. The process according to claim 10, wherein the bacterial spores are of *Bacillus pseudofirmus* or *Sporosarcina pasteurii*.

12. The process according to claim 1, wherein the organic compounds comprise an organic biomineral precursor compound and organic bacterial growth factors.

13. The process according to claim 12, wherein the organic biomineral precursor compound comprises an organic calcium or sodium salt and the organic bacterial growth factors comprise yeast extract or peptone.

14. The process according to claim 1, wherein the particle surface pore width is 0.01-1 μm.

* * * * *